United States Patent [19]

Baranczuk et al.

[11] Patent Number: 4,882,141

[45] Date of Patent: * Nov. 21, 1989

[54] TISSUE IMAGING UTILIZING LABELLED STEROIDS

[75] Inventors: Richard J. Baranczuk, Overland Park; Jay A. Spicer, Kansas City, both of Kans.

[73] Assignee: Bio-Medical Research Laboratories, Inc., Overland Park, Kans.

[ * ] Notice: The portion of the term of this patent subsequent to Apr. 21, 2004 has been disclaimed.

[21] Appl. No.: 118,237

[22] Filed: Nov. 6, 1987

Related U.S. Application Data

[63] Continuation-in-part of Ser. No. 663,572, Nov. 22, 1984, abandoned, and a continuation-in-part of Ser. No. 12,254, Feb. 9, 1987, which is a continuation-in-part of Ser. No. 663,600, Nov. 22, 1984, Pat. No. 4,659,517.

[51] Int. Cl.$^4$ .......................... A61K 49/02; C07J 00/00
[52] U.S. Cl. .................................... 424/1.1; 260/397.5; 424/9
[58] Field of Search .................. 424/1.1, 9; 260/397.4, 260/397.5

[56] References Cited

U.S. PATENT DOCUMENTS

| | | |
|---|---|---|
| 2,855,413 | 10/1958 | Mueller . |
| 3,784,576 | 1/1974 | Counsell . |
| 3,859,429 | 1/1975 | Elias . |
| 3,959,455 | 5/1976 | Ansari et al. . |
| 4,041,145 | 8/1977 | van der Veek . |
| 4,048,297 | 9/1977 | Counsell et al. . |
| 4,062,733 | 12/1977 | Edwards et al. . |
| 4,279,887 | 7/1981 | Baldwin et al. . |
| 4,290,965 | 9/1981 | Stocklin et al. . |
| 4,298,591 | 7/1981 | O'Brien, Jr. et al. . |
| 4,331,647 | 5/1982 | Goldenberg . |
| 4,465,676 | 8/1984 | Hochberg ........................ 424/238 |
| 4,659,517 | 4/1987 | Spicer et al. .................... 424/1.1 X |

OTHER PUBLICATIONS

Huffman, M. N., and Lott, M. H.; "16–Substituted Steroids, IV. 16–Keto–Alpha–Estradiol and 16–Ketoestrone", J. Biol. Chem. 172, 325 (1948).
Leeds, N. S., Fukushima, D. K. and Gallagher, T. F., "Studies of Steroid Ring D Epoxides of Enol Acetates; A New Syntheses of Estril and of Androstane–3–beta, 16–alpha, 17–beta–triol"; J.A.C.S., 76, 2943 (1954).
Soloway, A. H., Consedine W. J., Fukushima, D. K. and Gallagher T. F.; "Some Reactions of Epoxides of Steroid Enol Acetates", J.A.C.S., 76, 2941 (1954).
Fishman, J. & Biggerstaff, W. R., "Synthesis of 1,3,5(10)–Estratriene–3, 16–beta, 17–alpha-triol," J. of Org. Chem., 23, 1190 (1958).
Mueller, G. P. & Johns, W. F.; "16–alpha–chloro–and 16–alpha Iodo Estrone Meithyl Ether, New and Potent Lipid–Shifting Agents", J. Am Chem. Soc., 80, 1769 (1958).
Fakjas, J.; "Steroids, Part XLIII Comparison of the 16–Bromo–17–ketones and 16–Bromo–17–Alcohols in the 3–Unsubstituted and 3–beta–Oxygenated 5–alpha–Androstane Series", J. Chem. Soc., 3966 (1959).
Fieser, L. F. and Fieser, M., "Steroids", Reinhold Publishing Corp. New York (1967), p. 478.
Fishman, J.; "Rearrangement of Steroidal Ring D. Ketols", J.A.C.S., 82, 6143 (1960).
Mueller, G. P. & Johns, W. F., "The C–16 Halides of Estrone Methyl Ester" J. Org. Chem., 26, 2403 (1961).
Fishman, J.; "The Synthesis and Nuclear Magnetic Resonance Spectra of Epimeric 16–Deuterio–17–beta––and –17–alpha–estradiols", J.A.C.S., 87, 3455 (1965).
Hansen, R. L., "Perfluoroalkanesulfonate Esters as Alkylating Agents", J. Org. Chem., 30, 4322 (1965).
Su, Tah Mun Sliwinski, W. F. Schleyer, Paul von R., "The Solvolysis of Highly and Unreactive Substrates Using the Trifluoromethanesulfonate (Triflate) Leaving Group", J.A.C.S., 91, 5386 (1969).
Anderson, W. K. and Veysoglu, T.; "A Simple Procedure for the Epoxidation of Acid–Sensitive Olefinic Compounds with M–Chloroperbenzoic Acid in an Alkaline Biphasic Solvent System"; J. Org. Chem, 38, No. 12, 2267 (1973).
Beard, C. D., Baum, K. & Grakauskas, V., "Syntheses of Some Novel Trifluoromethanesulfates and Their Reactions with Alcohols", J. Org. Chem., 38, No. 21, 3673 (1973).
Howells, R. D. & McCown, J. D. "Trifluoromethanesulfonic Acid & Derivatives;" Chemical Reviews, 77, No. 1, 69 (1977).
Baranczuk, R. J., "What's the Catch?"Estrogen Receptor Interaction; Diagnostic Medicine, 1978.
Baranczuk, R. J., "A New Tool in the Fight to Control Advanced Breast Cancer", Diagnostic Medicine, 1978.
Arunachalam, T., Longcope, C., and Caspe, E., "Iodo-estrogens, Syntheses and Interaction with Urine Receptors,"J. Bio Chem. 254, No. 13, 5900 (1979).
Hochberg, R. B., "Iodine–125–Labeled Estradiol: A Gamma–Emitting Analog of Estradiol That Binds to the Estrogen Receptor", Science, 205, 1138 (1979).
Hochberg, R. B., and Rosner, W.; "Interaction of 16-Alpha-[$^{125}$I]iodo-Estradiol with Estrogen and (List continued on next page.)

*Primary Examiner*—John S. Maples
*Attorney, Agent, or Firm*—Litman, McMahon & Brown

[57] ABSTRACT

A process for detecting a presence of steroid receptors in tissue therapeutically and for treating certian tissue, especially tissue having estrogen receptors, includes the step of treating the tissue by injection, surface application or the like, with a labeled steroid. The labeled steroid may include a moiety which is readily imageable on a gamma radiation detector, on x-ray film, on a fluoroscope, through NMR devices or the like. An especially suitable labeled steroid has been found to be 16-$^{123}$I-17-beta-estradiol having a specific activity of greater than 2,000 curies per millimole and preferably at least 5,000 curies per millimole.

9 Claims, No Drawings

OTHER PUBLICATIONS

Other Steroid-Binging Proteins"; Proc. Natl. Acad. Sci. USA, 77, No. 1, 328 (1980).

Heiman, D. F., Senderoff, S. G., Katzenellenbogen, J. A. and Neeley, R. J. "Estrogen Receptor Based Imaging Agents, 1, Synthesis and Receptor Binding Affinity of Some Aromatic and D-Ring Halogenated Estrogens"; J. Med. Chem., 23, 994 (1980).

Longcope, C., Arunchalem, T., Rafkind I. and Caspi, E., "Biological Activity of [$^{127}$I]and [$^{125}$I] Estradiol Analogs In Vitro and In Vivo"; Journal of Steroid Biochemistry, 14, 261 (1981).

Katzenellenbogen, J. A., Senderoff, S. G., Carlson, K. E., McElwaney, K. D. and Welch, M. J., "Gamma-Emitting Estrogens; Development of Imaging Agents for Breast Tumors (Meeting Abstract("; Journal of Steroid Biochemistry, (1981). It is believed that the article is that referred to as reference 24 below.

Katzenellenbogen, J. A., "The Development of Gamma-Emitting Hormone Analogs as Imaging Agents for Receptor-Positive Tumors", The Prostatic Cell: Structure and Function, Part B, 313-327 (1981).

Argentini, M., Zahner, M., and Schuberger, P. A.; "Comparison of Several Methods for the Syntheses of W-Iodine-123-Hepta-Decanoic Acid", Journal of Radioanalytical Chemistry, 65, No. 1-2, 131 (1981).

McElvaney, K. D., Carlson K. E., Welch, M. J., Senderoff, S. G., Katzenellenbogen, J. A. and the Los Alamos Medical Radioistrope Group; "In Vivo Comparison of 16-Alpha-[$^{77}$Br] Bromoestradiol-17-beta and 16-alpha[$^{125}$I] Iodoestradiol-17-beta,", Journal of Nuclear Medicine, 23, 420 (1982).

McElvaney, L. D., Katzenellenbogen, J. A., Shafer, K. E., Siegel, B. A., Senderoff, S. G., Welch, M. J. and the Los Alamos Medical Radioisotope Group; "16-alpha. [$^{77}$Br] Bromoestradiol; Dosimetry and Preliminary Clinical Studies"Journal of Nuclear Medicine, 23, 425 (1982).

Oxley, D. K., Haven, G. T., Wittliff, J. K. and Gelbo, D.; "Precision in Estrogen and Progesterone Receptor Assays, Results of the First CAP Pilot Survey", A.J.C.P. 78, 587 (1982).

Duffy, M. J. "Short Communication Assay of Estradiol Receptors in Human Breast Carcinomas Using the Gamma Emitting Ligand 16-alpha [$^{125}$I] Iodoestradiol", Journal of Steroid Biochemistry, 16, 343 (1982).

Therain, F., Gros, J. and Souchu, A.; "Synthese du $^{123}$I-16 iodo estradiol", Journal de Biophysique et de Medecine Nucleaire, 6, 155 (1982). Translation Attached.

Landvatter, S. W., Katzenellenbogen, J. A., McElvaney, K. D. and Welch, M. J.; "Preparation and Properties of Halogenated Estrogens as Imaging Agents for Breast Tumors" Symposium Abstracts, Journal of Labelled Compounds and Radiopharmaceuticals, XIX, Nos. 11-12, 1293 (1982).

McElvaney K. D., Carlson, K. E., Katzenellenbogen, J. A., and Welch, M. J.; "Factors Affecting the Target Site Uptake Selectivity of Estrogen Radiopharmaceuticals: Serum Binding and Endogenous Estrogens", Journal of Steroid Biochemistry, 18, No. 6, p. 635 (1983).

The Radiopharmaceutical Science Council Newsletter, Fall, 1984, pp. 13-14.

Chemical Abstracts, vol. 98, No. 25, Jun. 20, 1983, p. 586, No. 2158786, Therain et al.

Journal Biological Chemistry, vol. 254, No. 13, 1979, p. 5900-5925; Thangavel et al.

Journal of Organic Chemistry, vol. 49, No. 25, Dec. 14, 1984, pp. 4900-4905; Kiesewitter et al.

Journal Nuclear Medicine, 23, pp. 420-424 (1982).

TISSUE IMAGING UTILIZING LABELLED STEROIDS

CROSS-REFERENCE TO RELATED APPLICATIONS

The present application is a continuation-in-part of U.S. Ser. No. 663,572 filed Nov. 22, 1984 of the same title, now abandoned and is also a continuation-in-part of U.S. Ser. No. 012,254 filed Feb. 9, 1987 entitled HALOGEN LABELED COMPOUNDS INCLUDING ESTRADIOL DERIVATIVES, THEIR SYNTHETIC INTERMEDIATES AND THE SYNTHESES THEREOF which was a continuation of Ser. No. 663,600 filed Nov. 22, 1984, now U.S. Pat. No. 4,659,517, both of the latter being incorporated herein by reference.

BACKGROUND OF THE INVENTION

Certain research related to the subject matter of the present application was conducted under monetary grants from the United States of America and a paid up, nonexclusive, irrevocable and non-transferrable license is hereby granted to the United States of America for governmental purposes.

The present invention relates to imaging, detection or treatment of tissue with labeled steroids and, in particular, to imaging of a living internal tissue by treatment of the tissue with a 16-$^{123}$I-estradiol.

Medical science has often found the use of non-invasive techniques to study various tissues within a body to be very helpful in diagnosis of various diseases or injuries. For this purpose, various detectable materials have been developed over the years which are designed to be applied to living tissue to be studied, so as to provide an image of the tissue outside of the body. Preferably, such materials bind with the particular tissue to be studied. It has also been found that such imaging materials often help in studying tissues outside of a body, as for example in assays in which an amount of binding site present is measured. Thus, the detectable materials are often usable for both in vivo and in vitro studies.

Various detectable materials are imageable or detectable in different ways. For example, some materials that have been suggested for imaging or assay purposes release radiation which can be detected. Other materials are suitable for detection by nuclear magnetic resonance (NMR) devices or the like.

One of the major limitations on materials used for detection within living animals is that the material should be relatively benign to the animal host. Therefore, although high concentrations of strongly radioactive materials may often provide a good imaging source, they are not generally compatible with use in living tissue. In addition, where a carrier mechanism is utilized to preferentially carry the detectable material to a particular tissue of interest, certain labels may render the carrier generally ineffective in preferentially binding to that particular tissue or the receptors therein to be studied.

Steroids have been heavily studied for use as carriers for detectable materials. One particularly effective group of steroids has been estrogen and its derivatives, which seek out organs in the body having estrogen receptors, including such organs as the ovaries, cervix, uterus, breast, and brain. Suitable estrogen receptors are also sometimes present in some types of cancerous lung tissue, as well as skin, bones, and testes.

Various halogens have often been suggested as effective detectable agents, since the halogens often are readily combinable with estrogen. While certain combinations of estrogens and halides may affect the binding ability of an estrogen carrier, certain other combinations do not substantially modify the binding ability of the estrogen with estrogen receptors. One particular type of halogen that has been proposed as a label is radioactive iodine. For example, Hochberg has developed a process to make estrogens labled with iodine 125.

Problems have arisen, however, with the use of iodine, even though the affect of iodine and iodinated steroids in animals has been heavily studied. One of the major problems associated with the use of certain common radioactive isotopes of iodine has been that they often do not have sufficient energy associated with their radioactive decay to substantially penetrate the animal body, when used in vivo, and consequently do not provide clear images on a detector. In addition, the readily available radioactive isotope $^{125}$I has a fairly long half-life and it is generally not desirable to place long half-life radioisotopes within an animal body, since damage from radioactivity is more likely to occur with the longer lived isotopes. Also, a greater amount of the radioactive iodine may need to be injected when the half-life is long, in order to provide enough decay to be readily detectable.

Iodine isotope I-123 substantially overcomes the problem with the long half-life, since it has a half-life of only approximately 13.3 hours; and, further has a fairly high energy gamma radiation decay, generally making it readily detectable. In addition, it is found that images produced by $^{123}$I decay are generally sharp or clear. Unfortunately, the short half-life of $^{123}$I has effectively prevented previous use of $^{123}$I-iodinated estradiols, since conventional methods of producing them have typically taken between 20 to 40 hours, conventional methods of synthesis generally produce mixtures, and conventional syntheses have generally led to relatively low yields. Thus, by the end of the production of the $^{123}$I-iodonated estradiol, a substantial number of half-lives may have already run; and, especially if the yield is relatively low, the iodinated product may not be generally readily utilizable for imaging or assays.

Estradiol iodonated with iodine-123 is now manufacturable within a two to four hour time period and will be available from Biomedical Research Labs of Lenexa, Kan., the assignee of the present application, or through its licensees. A synthesis for the production of estradiol iodinated with iodine-123 suitable for use with the methods of the present invention is disclosed in U.S. Pat. No. 4,659,517 which is incorporated herein by reference. The present application is indirectly a continuation-in-part of this issued patent.

With general availability of the estradiol effectively iodonated with the I-123 isotope, there has been a desire to produce imaging methods for utilization of the I-123 compound.

OBJECTS OF THE INVENTION

Therefore, the objects of the present invention are: to provide a method of imaging or treating tissue, especially imaging selected animal body tissue as compared to other tissue within the animal; to provide such a method utilizing labeled steroids which are selectively targeted for body tissue having receptors for such steroids; to provide such a method wherein the steroid is an estrogen carrier suitably preferential for binding with various estrogen receptors in selective body tissue; to provide such a method wherein the label is a halogen, in particular, radioactive iodine-123; to provide such a method which allows assay or imaging of tissue both in vitro and in vivo; to provide such a method utilizing an $^{123}$I estradiol composition, which has a relatively high specific activity and which is sufficiently concentrated to permit use of sufficient radioactive iodine to provide suitable imaging, and yet not have a substantial amount of non-radioactive estradiol present; to provide such a method which is easy to use and particularly well adapted for the proposed usage thereof.

Other objects and advantages of this invention will become apparent from the following description taken in conjunction with the accompanying drawings wherein are set forth, by way of illustration and example, certain embodiments of this invention.

SUMMARY OF THE INVENTION

A method is provided for binding detectable labels to receptors so as to allow imaging of their locations in various tissue, as compared to surrounding tissue. The imaging is especially effective on living tissue and generally results in little substantial damage to the tissue. Also, the method can be used to determine certain features about certain tissues within a living body without invasive surgery. The method includes application of a detectable labeled material to the tissue to be studied. The application may be by intravenous or subcutaneous injection, by oral administration, or by application to a surface, such as by vaginal douche or the like. For detection of receptors in non-living tissue, application may be directly to the surface thereof or on homogenization therewith.

Preferably, the method includes the application of a labeled steroid to the tissue such that the labeled steroid becomes joined or bound to certain binding cites or receptors in a specific tissue, in preference to other locations in the surrounding tissue or in other parts of the body. After binding, suitable detection or imaging techniques can be used to analyze the presence of the receptors at the binding sites.

For example, estrogen-receptor-active estrogens will generally selectively bind to that tissue which has relatively greater quantities of such estrogen receptors. It is noted that in certain early stages of cancer, at least for certain types of tissue, there has been found to be a stage in which there are more estrogen receptors present than are present in normal, healthy tissue. The relatively high level of estrogen receptors in these cancerous tissues or tumors and metaseses continues until the cancer reaches a certain stage in its development, after which the relative quantity of estrogen receptors therein are generally observed to become substantially reduced. The early rapid increase in the number of estrogen receptors, in cancerous tissue, may allow labeled estrogen to be used to image such cancerous tissue, or the tumors therein, to distinguish the cancerous portion from surrounding healthy tissue. This generally allows simple and rapid determination of the location of the original tumor and any metasteses thereof as well as a potentially easy determination of whether chemotherapy-type treatment or the like is likely to be effective in reducing or retarding additional tumor growth. Also, the decrease or complete absence of estrogen receptors in a known tumor may appear as a non-image, which may form medical personnel that the tumor has undergone modification and that a change of treatment is probably warranted. Further, if detection is by count, rather than imaging, then regardless of whether the detection is conducted in vivo or in vitro, the assay performed may lead to a relatively rapid determination of the relative amount of receptor present, so as to aid in certain diagnoses.

It is foreseen that such imaging may be particularly useful to image areas for determination of where surgical removal of tissue will be desired. For example, if the patient is diagnosed to have breast cancer, the imaging may indicate what portion should be removed during surgery.

It is foreseen that the labeled steroid may be any of a variety of steroids and that the label may be any of a variety of imageable materials which can be easily detected. For example, concentrations of estrogen receptor active estrogens labeled with fluorine may be imaged by use of nuclear magnetic resonance (NMR) devices which can detect the presence of certain fluorine nucleii. Certain radioactive halogens may also be utilized for imaging depending on whether the imaging is to be on the surface of the tissue or internal. In the latter case, the radiation energy of the radioactive decay should be sufficient to substantially penetrate the surrounding body and give clear images on a detector.

As used herein, the term estrogen refers to any of the estrogen-receptor-active estrogen derivatives, and in particular to estradiol. The binding affinity of the labeled estradiol, for estrogen receptors, may vary considerably from that for estradiol itself and still be substantial enough for reliable detection. The 16-$^{123}$I-17-beta-estradiols have been found to be a class of particularly effective labeled steroids. 16-alpha-iodinated-17-beta estradiol is likely to be slightly more effective in binding than the 16-beta-iodinated-17-beta-estradiol, since it has a somewhat greater affinity for estrogen receptors, although both are fairly close in efficiency in binding with estrogen receptor sites and it is foreseen that either may be effective.

Preferably, I-123-labeled estradiol used is relatively free from by-products and precursors, immediately following its manufacture. By having a relatively pure labeled estrogen material, fewer non-labeled estrogens, or undesired labeled estrogen derivatives, are present with the desired labeled estrogens, to compete therewith for estrogen receptor sites. If too many unlabeled estrogens are present within the material, too few desirably labeled estrogens may be able to bind to the estrogen receptor sites, at the location where imaging is desired, to provide a satisfactory image on detection equipment. Further, side products or contaminants may have an affinity for binding sites other than estrogen receptors and could lead to unreliable assay results, particularly if they cause detectable label to appear at non-estrogen receptor sites. Further, even the preferred 16-$^{123}$I-17-beta-estradiols may have some affinity for sites that are not desired to be imaged, and could, in time, bind to or be captured by such sites if they lose in competition for estrogen receptor binding sites with the side products or contaminants.

Small doses of the labeled estrogen are also preferably used, so that not all of the receptor sites in the body will be occupied. A reason for this is that, if excess labeled estrogen is present, quantities of a labeled estrogens may circulate in the blood and effectively show as a single image throughout the entire body, or they may partially blur or blind the actual tissue which is desired to be imaged.

Preferably, where a radioactive component is used, the specific activity is relatively high so that a small quantity can provide sufficient radiation for detectable images. When I-123 estradiol is utilized a specific activity substantially greater than 2,000 curies per millimole and preferably at least 5,000 curies per millimole is desired. Generally, higher specific activities are feasible if the iodinated estradiol is utilized relatively soon after manufacture thereof. As used herein, specific activity refers to the radioactive decay of a quantity of the labeled material only. Thus, when labeled material is placed in a carrier solution for injection, the specific activity value remains unchanged.

For imaging, the dosage for use in mammals is foreseen to be typically in a range from one-half to ten millicuries. It is foreseen that higher doses are feasible when the labeled material is to be used for therapeutic rather than simple imaging purposes. Generally, for imaging, doses on the order of one-half to two millicuries are preferable for most purposes. Normally, the labeled estrogen will be diluted, with a solvent, to approximately between one and ten millicuries per milliliter, so that a relatively high amount of radioactively decaying material may be contained in relatively small volume, in order to make injection simpler and to avoid dispersion of the label over too great a volume during injection. When injection is the method of utilization of the imaging material, a suitable carrier fluid, or diluent, for the labeled material, is a mixture, by volume, having about 95% of a normal saline solution and about 5% of 95% ethanol. Certain adjustment may be made if the particular steroid used has a low solubility in water.

When imaging, normally the time frame during which binding or joining occurs, in order to reach a detectable or an optimal imaging level, varies depending upon what is to be imaged and the labeled material. Very soon after injection of some steroids, the gallbladder and gut of the subject animal will typically quickly collect a large amount of the material. Such collection is normally not associated with the steroid binding to a receptor.

Detectable images due to binding at receptors are often present very quickly and normally within one-half to two hours after injection of labeled material into a body. However, longer periods of time may sometimes be necessary to let areas like the gut become relatively clear of the imaging material, so that other organs aligned with the gut become more visible. Sometimes the bowel must be cleaned of degradation products of labeled materials from the gut in order to remove partly degraded but still labeled, material that had originally entered the gut and generally enable ready detection of images on either side thereof.

It is foreseen that under certain conditions it may be desirable to flood the body with non-radioactive label prior to injection of radioactively labeled steroid material. For example, when radioactive iodine is incorporated into the steroid, it may be desirable to first increase the level of free iodine within the body being treated, so that the thyroid is somewhat saturated with non-radioactive iodine, and therefore less likely to pick up radioactive iodine resulting from degradation of the labeled steroid material.

As was previously mentioned, it is foreseen that it is feasible to use the concepts of the present invention, especially the I-123 labeled estradiol material, for imaging of non-living tissue or the like. One usage of such material is in autoradiography. Conventionally for this procedure a slice of tissue is placed upon a slide and allowed to mix with a steroid carrier having tritium attached thereto, washed and retained tritium bound to receptors is allowed to expose a photographic emulsion. However, such a process is very slow often taking many months.

In accordance with the present invention a receptive carrier labeled with iodine 123 may be utilized for this purpose. For example, a tissue having estrogen receptors is coated with an I-123-estradiol after which excess estradiol is washed away. A photographic emulsion is then placed on the surface of the tissue and allowed to develop.

Steroid material having a therapeutic label may be utilized for treatment of a tissue in a body. For example, a radioactive label may be utilized to provide radioactive treatment of a cancerous tumor at the site of the tumor.

DETAILED DESCRIPTION OF THE INVENTION

As required, detailed embodiments of the present invention are disclosed herein; however, it is to be understood that the disclosed embodiments are merely exemplary of the invention which may be embodied in various forms. Therefore, details disclosed herein are not to be interpreted as limiting, but merely as a basis for the claims and as a representative basis for teaching one skilled in the art to variously employ the present invention in virtually any appropriate application.

In accordance with the present invention, methods are provided for imaging a selected tissue, through detection means remote from such tissue, and for therapeutically treating such tissue. The imaging may be accomplished by detecting radioactive decay or by other detection methods such as NMR. In the present particular embodiment, an iodinated estradiol having a high percentage of iodine-123, especially as 16-alpha-I-123-17-beta-estradiol, is applied to a tissue to be imaged. For example, the imaging material is dissolved in one-half milliliter of a duluent comprising, by volume, 95% of normal saline solution and 5% of 95% ethanol, and is injected into a blood stream of an animal host to the particular tissue which is desired to be imaged. The imageable material is preferably selected to preferentially seek out certain receptors in the tissue and to bind thereto, for later detection.

Preferably, a small quantity of a radioactive material having a relatively high specific activity is used. Where I-123 labeled estradiol is utilized, it is preferred that the specific activity of the labeled steroid be at least 5,000 curies per millimole. Generally, the higher the specific activity the better, since small quantities must be used to produce the minimum radiation necessary to be detectable.

A theoretical upper limit on activity for the I-123 estradiol is about 237,000 curies per millimole. It is foreseen that the number of millicuries injected will vary with the body weight of the animal or person being administered the steroid. Also, the amount of radioactive substrate injected is foreseen to be variable depending upon the location and type of receptor involved, the intensity of image needed, and if therapy is intended, the therapeutic effect desired. It is expected that a normal usage in humans for imaging would be in the range of one-half to two millicuries, but this range may, for numerous reasons, vary substantially, as discussed above.

Following injection, detection will often be delayed to allow the imaging material to reach the desired tissue location where detection or therapy is to occur. After allowing the labeled material to bind to receptors, the animal or human subject is placed under an appropriate detector for the type of label used. For example, where gamma radiation is released, as by iodine 123, a suitable gamma raiation detector is positioned close to the body and over the tissue to be imaged. The detector effectively determines the pattern of radiation emission to image the tissue being studied. Where I-123 labeled estradiol is utilized, the I-123 fairly rapidly degrades due to the short half-life thereof. The estradiol is also eventually degraded by the body possibly even before the iodine totally decays.

The following example is for the purpose of illustration of the invention and should not be interpreted as limiting the scope of applicants' invention.

EXAMPLE 1

A plurality of laboratory rabbits are injected with 1.92 millicuries of I-123 estradiol. The $^{123}$I-estradiol is contained within and is administered within, an aliquot of solution. The diluent comprises a mixture, by volume, comprising 95% of normal saline solution and 5% of 90% ethanol. The I-123-labeled estradiol had an apparent specific activity in excess of 30,000 curies per millimole. A gamma radiation detector was placed immediately exterior to each of the rabbits, and over a region directly adjacent the ovaries and uterus. Within a few minutes the detector was able to begin to show an outline of the uterus. After about one-half hour images of the uterus and ovaries were readily detectable. Slight improvements in the images were seen over the next few hours. The ovaries and uterus of each of the rabbits was clearly visible against the other body organs of the associated rabbit.

It is to be understood that while certain forms of the present invention have been illustrated and described herein, it is not be limited to the specific processes, forms or compositions described.

What is claimed and desired to secure by Letters Patent is as follows:

1. A method of imaging a tissue in vivo, said tissue having steroid receptors present therein; said method comprising the steps of:
   (a) applying a labeled steroid material to said tissue; said material including 16-$^{123}$I-17-beta-estradiol; said material having a minimum specific activity of 5,000 curies per millimole and upon decay releasing radiation of sufficient energy to penetrate said body;
   (b) allowing a portion of said labeled steroid material to substantially join with said receptors in said tissue; and
   (c) thereafter obtaining an image of said labeled steroid material in said tissue by utilization of detection means appropriately positioned to detect said radiation from said radioactive component.

2. The process according to claim 1 wherein:
   (a) said body is a human body and including the step of:
   (b) injecting an amount in the range from about 0.5 to about 10.0 millicuries of said labeled steroid material into said body.

3. The method according to claim 2 wherein:
   (a) said estradiol is 16-beta-$^{123}$I-17-beta-estradiol and said injected amount is betwen 0.5 and 2 millicuries.

4. The method according to claim 2 wherein:
   (a) said labeled steroid material is allowed to join with said receptors for a time period of between about 0.5 to about 24 hours.

5. The method according to claim 2 wherein:
   (a) said specific activity is greater than 30,000 curies per millimole at the time said material is applied to said tissue.

6. A method of imaging a tissue within a human body wherein said tissue includes estrogen receptors; said method comprising the steps of
   (a) applying an $^{123}$I labeled estradiol substantially comprising 16-$^{123}$I-17-beta-estradiol to said tissue; said $^{123}$I labeled estradiol having a specific activity at a time of application to said body of at least 5,000 curies per millimole;
   (b) allowing a substantial portion of said $^{123}$I labeled estradiol to join with said receptors;
   (c) utilizing gamma radiation detection means outside said body to detect a location and relative strength of radiation radiating from said tissue so as to allow imaging thereof.

7. The method according to claim 6 including the step of:
   (a) injecting between about 0.5 and about 10.0 millicuries of said $^{123}$I labeled estradiol into said body.

8. A method of therapeutically treating a tissue within a human body wherein said tissue includes estrogen receptors; said method comprising the steps of:
   (a) injecting a material including an $^{123}$I labeled estradiol substantially comprising 16-$^{123}$I-17-beta-estradiol into said body; said $^{123}$I labeled estradiol having a specific activity, at a time of application to said body, of at least 5,000 curies per millimole; and
   (b) allowing said $^{123}$I labeled estradiol to substantially join with said receptors.

9. The method according to claim 8 wherein:
   (a) at least 0.5 millicuries of said $^{123}$I labeled estradiol are injected into said body.

* * * * *